United States Patent [19]

Dorn et al.

[11] Patent Number: 5,032,688
[45] Date of Patent: Jul. 16, 1991

[54] PROCESS FOR THE PREPARATION OF ARALKYL HYDROPEROXIDES

[75] Inventors: Maximilian Dorn, Pullach; Eberhard Hägel, Icking; Werner Zeiss, Gröbenzell, all of Fed. Rep. of Germany

[73] Assignee: Peroxid-Chemie GmbH, Hoellriegelskreuth, Fed. Rep. of Germany

[21] Appl. No.: 432,781

[22] Filed: Nov. 7, 1989

[30] Foreign Application Priority Data

Nov. 9, 1988 [DE] Fed. Rep. of Germany ....... 3838028

[51] Int. Cl.$^5$ .................. C07C 409/08; C07C 409/12
[52] U.S. Cl. ...................................... 568/568; 568/569
[58] Field of Search ............................... 568/568, 569

[56] References Cited

U.S. PATENT DOCUMENTS 2,829,173  4/1958  Shiffler et al. ...................... 568/569

FOREIGN PATENT DOCUMENTS 63-309858  12/1988  Japan ................................. 568/568

OTHER PUBLICATIONS

Van Steveninck et al., *Rec. trav. Chem.*, 79: 413-429 (1980).

*Primary Examiner*—Werren B. Lone
*Assistant Examiner*—Margaret Argo
*Attorney, Agent, or Firm*—Felfe & Lynch

[57] ABSTRACT

A process for the preparation of aralkyl hydroperoxides having the formula (I) is described

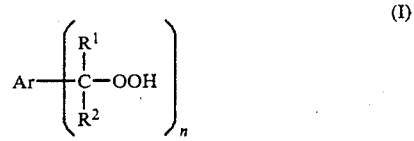

in which n=1, 2 or 3, Ar means a phenyl group which can be substituted with halogen or one or more branched or straight chain alkyl groups with 1 to 5 C-atoms, or a naphthyl group, and each radical $R^1$ and $R^2$ means a low alkyl radical, the alkyl radicals $R^1$ and $R^2$ together having 2 to 4 carbon atoms, by reaction of aralkyl carbinols having the formula (II)

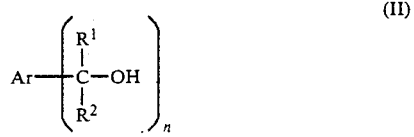

in which Ar, $R^1$, $R^2$ and n have the meaning given for formula (I), with hydrogen peroxide under acid conditions, the reaction being carried out in the presence of an acid-combining agent. An alkali sulphate, ammonium sulphate, alkali hydrogen sulphate and/or ammonium hydrogen sulphate is used in preference as the acid-combining agent. Tert.aralkyl hydroperoxides can be prepared in high yield with a high purity in a simple and safe manner with this process.

10 Claims, No Drawings

PROCESS FOR THE PREPARATION OF ARALKYL HYDROPEROXIDES

FIELD OF THE INVENTION

The invention relates to a process for the preparation of aralkyl hydroperoxides.

BACKGROUND OF THE INVENTION

Hydroperoxides are used in many ways in the chemical industry and engineering, e.g. as catalysts or curing agents in polymerization reactions, as sources of oxygen in blowing agents and as intermediates for the preparation of the corresponding alcohols of peroxides and peracid esters. In this respect, tert.aralkyl hydroperoxides in particular are of great importance.

Tert.aralkyl hydroperoxides are generally prepared by oxidation of the corresponding hydrocarbons with molecular oxygen, conversion rates of only 30 to 35% being obtained; at higher conversion rates, the selectivity falls considerably, i.e. by-products are formed to an increasing degree. The hydroperoxides must then be concentrated by distillation, crystallization or extraction, or separated from unreacted hydrocarbon starting product.

Two methods for the preparation of tert.hydroperoxides by reaction of tert.alcohols with hydrogen peroxide with acid catalysis are known from the literature, which processes operate with different concentrations and quantities of sulphuric acid: R. Criegee and H. Dietrich (Annalen 560 (1948) 135) operate using 80 to 95% $H_2O_2$ and in the presence of low concentration sulphuric acid; and Milas and Harries (J.Am.Chem Soc. 60 (1938) 2434) operate using 30% $H_2O_2$ in the presence of a large quantity of 70% sulphuric acid. The process according to R. Criegee and H. Dietrich is described by the authors themselves as unsuitable for relatively large batches, and it is admitted that the older process according to Milas and Harries is cheaper and safer and is, therefore, the only one suitable for relatively large batches. The procedure according to Milas and Harries does, however, have disadvantages in the case of the preparation of tert.aralkyl hydroperoxides; these hydroperoxides are very sensitive to strong acids and decompose into ketones and phenols.

According to M. S. Belenkiy et al (The Soviet Chem.Ind. 1 (1972) 16), aryl-alkyl-carbinols contained in mixtures obtained from the oxidation of alkyl aromatics with air are oxidized with hydrogen peroxide to the hydroperoxides. High conversion rates and, hence, good yields can be achieved only if high temperatures and/or relatively high acid concentrations are used. The optimum conditions stated represent a compromise between the formation and decomposition of the hydroperoxides.

A. Burghardt et al (Chemia Stosowana, Ser. A, Volume 13, No. 4 (1969) 335-342) describe the reaction of methyl ethyl phenyl carbinol with hydrogen peroxide in the presence of sulphuric acid and a solvent to sec.-butylbenzene hydroperoxide; due to the large quantity of non-polar solvent (four times the amount of carbinol), the hydroperoxide formed is protected from decomposition by acid.

According to A. Burghardt et al (Zess.Nauk.-Politech.Slask., Chem. No. 60 (1972) 3-20), cumene hydroperoxide is prepared from dimethylphenyl carbinol and hydrogen peroxide in the presence of a solvent. Sulphuric acid and/or acid cation exchangers are used as acid catalyst. With this process, too, operations are not carried out without solvent and no pure hydroperoxide is produced. If a solid hydroperoxide were prepared, separation of the ion exchange resin would also be extremely difficult.

Even in the applicant's own tests for the preparation of the hydroperoxides in the pure form from pure carbinols with $H_2O_2$/mineral acid, there was an insufficient reaction and, hence, a low yield and purity of the product, or a tendency towards decomposition which leads to considerable discoloration of the product. The acid catalyzed decomposition of tert. aralkyl hydroperoxides is, moreover, highly exothermic and therefore also represents a high safety risk.

OBJECTS OF THE INVENTION

The task of the present invention was, therefore, to provide a process for the preparation of tert.aralkyl hydroperoxides with which the above mentioned disadvantages can be avoided and with which it is possible to prepare the tert.aralkyl hydroperoxides in high yield and with high purity in a simple and safe manner. This task is solved with the process according to the invention.

DESCRIPTION OF THE INVENTION

The subject of the invention is a process for the preparation of aralkyl hydroperoxides having the formula (I).

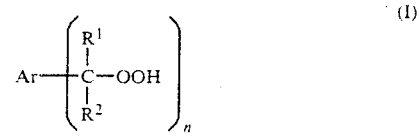

in which n=1, 2 or 3, Ar means a phenyl group which can be substituted with halogen or one or more branched or straight chain alkyl groups with 1 to 5 C-atoms, or a naphthyl group, and each radical $R^1$ and $R^2$ means a lower alkyl radical, the sum of the carbon atoms in the alkyl radicals $R^1$ and $R^2$ being inclusive, by reaction of aralkyl carbinols having the formula

in which Ar, $R^1$, $R^2$ and n have the meaning given for formula (I), with hydrogen peroxide under acid conditions, which is characterized in that the reaction is carried out in the presence of an acid-binding agent.

Surprisingly, it has become apparent that aralkyl hydroperoxides having formula (I) can be prepared in high yields and with very good purity by reaction of aralkyl carbinols having the formula (II) with hydrogen peroxide under acid conditions, if the reaction is carried out in accordance with the invention in the presence of an acid-binding agent. No spontaneous decomposition occurs, as a result of which the process can also be carried out safely.

Generally speaking, any acid-binding agent which does not affect the reaction, i.e. which is inert with respect to the reactants can be used as acid-binding agent. Such acid-binding agents are inorganic or organic compounds which can act as proton acceptors because of their dissociation equilibrium in the acid reaction medium. Representative examples of these are, for example, salts of inorganic or organic acids with metals, particularly alkali metals or ammonium, or with organic cations such as, for example, tetra alkyl ammonium salts. Of these compounds, phosphates, e.g. alkali phosphates or ammonium phosphates, borates, e.g. borax, carboxylates, e.g. sodium acetate or ammonium acetate, ureas etc. should be mentioned in particular. Alkali sulphates, particularly sodium sulphate, ammonium sulphate, alkali hydrogen sulphates, particularly sodium hydrogen sulphate and/or ammonium hydrogen sulphate are particularly advantageous and should, therefore, be mentioned in preference. Mixtures of two or more acid-binding agents can also be used, e.g. a mixture of sodium sulphate and sodium hydrogen sulphate.

It is preferable to operate in the presence of 1 to 5 mols hydrogen peroxide per mole of hydroxyl group of carbinol and in particular with 2 to 3 mols hydrogen peroxide per mole OH group.

The hydrogen peroxide concentration in the aqueous phase is preferably 10 to 35% by weight and in particular 15 to 25% by weight. The aqueous phase is taken to mean the mixture (solution) of hydrogen peroxide, acid, the acid-binding agent (e.g. alkali or ammonium sulphate and/or alkali or ammonium hydrogen sulphate) in water.

The acids normally used in this field can be used as acid. Phosphoric acid, perchloric acid and sulphonic acid, for example, are suitable. Sulphuric acid is used in preference.

It is preferable to operate with an acid concentration in the aqueous phase of 1 to 10% by weight.

The temperature of the reaction is preferably between 15 and 70° C. and in particular 35 to 50° C.

The most advantageous molar ratio of acid to acid-binding agent is determined by the nature of the carbinol starting product to be reacted and the other reaction parameters (temperature, quantity and concentration of hydrogen peroxide and acid) and depends in particular on the nature of the acid-binding agent. As a rule, good results are obtained with a molar ratio of acid/acid-binding agent of ½ to 2/1. If a mixture of two or more acid-binding agents is used, e.g. sodium sulphate and sodium hydrogen sulphate, the ratio of the individual components of the mixture to each other can be important. For example, using a mixture of sulphate and hydrogen sulphate, the acid strength of the mixture can be varied if the ratio of sulphate to hydrogen sulphate is altered.

A mixture of sulphuric acid and an amount of a solution of alhalihydroxide or ammonia, which partly neutralizes said acid can be used instead of a mixture of sulphuric acid, and alkali or ammoniumsulphate.

The aralkyl hydroperoxides having the general formula (I) prepared according to the invention are generally solids at ambient temperature. Consequently, in order to obtain a certain consistency (stirrability) of the reaction mixture, it can be expedient to carry out the reaction in the presence of an inert diluent (desensitizing agent) and/or in the presence of an inert solvent. The susceptibility to explosion can also be reduced by the presence of a conventional desensitizing agent for such reactions.

High boiling aliphatic or aromatic hydrocarbons or phthalates such as dimethylphthalate or dibutylphthalate, for example, are suitable as inert solvents.

The quantity of diluent (desensitizing agent) and a solvent is chosen preferably in such a way that the hydroperoxide is obtained in the crystalline form and can readily be filtered; the solvent remaining in the solid hydroperoxide can also act as a desensitizing agent and thus increases the handling safety of the peroxide, as does the addition of an additional desensitizing agent. As a rule, it is sufficient to add the solvent in a quantity of approximately 5% by weight, based on the carbinol starting product.

The examples below are intended to explain the invention in more detail without restricting it thereto. Unless otherwise stated, the temperature details given above and below relate to the Celsius Scale and quantity details refer to parts by weight and weight per cent.

EXAMPLE 1

75 g ammonium sulphate are dissolved in 1350 g 18% hydrogen peroxide. After the addition of 60 g sulphuric acid (72%), 245 g 1,4-bis-(hydroxyisopropyl) benzene are added in portions at 25° C., with stirring, the mixture is heated to 50° C. and stirred at this temperature for 2 hours. After dilution with water, the mixture is cooled to 25° C., neutralized with dilute sodium hydroxide solution, the finished product is filtered and washed free of hydrogen peroxide.

703 g of a white, water-moist powder with a p-diisopropylbenzene dihydroperoxide content of 35.2%, corresponding to 87.5% of the theoretical, are obtained.

EXAMPLE 2

15 g dimethyl phthalate are added to a mixture of 1000 g 21% hydrogen peroxide, 30 g 72% sulphuric acid and 30 g ammonium sulphate, and 245 g 1,4-bis(hydroxyisopropyl) benzene are then added in portions at 25° C., with stirring, the mixture is heated to 40° C., and stirred at this temperature for 3 hours, the mixture becoming viscous during this operation. After cooling to 25° C., the reaction mixture is neutralized with dilute sodium hydroxide solution, the solid product is filtered and washed free of hydrogen peroxide.

640 g of a white, water-moist powder with a p-diisopropylbenzene dihydroperoxide content of 39.5%, corresponding to 89.4% of the theoretical, are obtained.

EXAMPLE 3

245 g 1,4-bis(hydroxyisopropyl) benzene are added in portions to a mixture of 1000 g 21% hydrogen peroxide, 53 g sodium hydrogen sulphate and 15 g dimethyl phthalate at 25° C., with stirring, the mixture is heated to 40° C., and stirred at this temperature for 3 hours. The viscous mixture is diluted with water, cooled to 25° C., and neutralized with dilute sodium hydroxide solution. The solid product is filtered off and washed free of hydrogen peroxide.

677 g of a white, water-moist product with a p-diisopropylbenzene dihydroperoxide content of 35.7%, corresponding to 85.4% of the theoretical, are obtained.

EXAMPLE 4 (COMPARATIVE EXAMPLE)

Operations are carried out as described in Example 2 except that no ammonium sulphate is added. Decomposition phenomena, manifested by the development of smoke, occur repeatedly during the post-stirring time.

In particular, splashes on the vessel wall decompose with the development of smoke and brown discoloration. After the product is filtered by suction, the mother liquor is yellowish-brown in color. 659 g of a grey, water-moist powder with a dihydroperoxide content of 34%, corresponding to 79.3% of the theoretical, are obtained.

We claim:

1. The method of preparing an aralkyl hydroperoxide of the formula

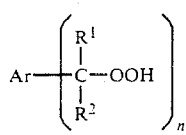  (I)

wherein n is 1, 2 or 3, Ar is a phenyl group which can be substituted with halogen or one or more branched or straight chain alkyl groups of 1 to 5 carbon atoms, or a naphthyl group, and each radical $R^1$ and $R^2$ is lower alkyl, the sum of the carbon atoms in the arkyl radicals $R^1$ and $R^2$ being from 2 to 4, inclusive, which comprises reacting an aralkyl carbinol of the formula

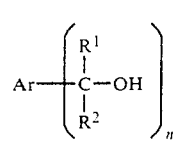  (II)

wherein Ar, $R^1$, $R^2$ and n have the meanings previously defined, with hydrogen peroxide under acid conditions, in the presence of an acid-binding agent.

2. The method of claim 1, wherein said acid-binding agent is an alkali metal sulphate, ammonium sulpahte, alkali metal hydrogen sulphate or ammonium hydrogen sulphate.

3. The method of claim 1, wherein said reaction is carried out with 1 to 5 mols of hydrogen peroxide per mol OH group in said carbinol.

4. The method of claim 1, wherein the hydrogen peroxide concentration in the reaction mixture is 10 to 35% by weight.

5. The method of claim 4, wherein the hydrogen peroxide concentration is 15% to 25% by weight.

6. The method of claim 1, wherein the acid concentration in the reaction mixture is 1 to 10% by weight.

7. The method of claim 1, wherein said acid is sulphuric acid.

8. The method of claim 12, wherein said molar ratio of acid/acid-binding agent is ½ to 2/1.

9. The method of claim 1, wherein said reaction is carried out at a temperature of 15° C. to 70° C.

10. The method of claim 1, wherein said reaction is carried out in the presence of an inert diluent, desensitizing agent or solvent.

* * * * *

UNITED STATES PATENT AND TRADEMARK OFFICE
CERTIFICATE OF CORRECTION

PATENT NO. : 5,032,688

DATED : July 16, 1991

INVENTOR(S) : Maximilian Dorn et al

It is certified that error appears in the above-identified patent and that said Letters Patent is hereby corrected as shown below:

Column 3, line 56, "alhalihydroxide" should read --alkalihydroxide--.

Column 6, line 28, "12" should read --1--.

Signed and Sealed this

Twenty-third Day of March, 1993

Attest:

STEPHEN G. KUNIN

*Attesting Officer*  Acting Commissioner of Patents and Trademarks